United States Patent
Mitchell et al.

(10) Patent No.: US 6,214,037 B1
(45) Date of Patent: Apr. 10, 2001

(54) RADIALLY EXPANDING STENT

(75) Inventors: Michael Edward Mitchell, Brookline; Gloria Miran Ro, Quincy; Aoy Tomita, Brookline, all of MA (US)

(73) Assignee: Fossa Industries, LLC, Quincy, MA (US)

( * ) Notice: Subject to any disclaimer, the term of this patent is extended or adjusted under 35 U.S.C. 154(b) by 0 days.

(21) Appl. No.: 09/272,660

(22) Filed: Mar. 18, 1999

(51) Int. Cl.[7] .................................................. A61F 2/00
(52) U.S. Cl. .................. 623/1.11; 623/1.11; 623/1.12; 623/1.23; 623/1.38
(58) Field of Search .................. 623/1.11, 1.12, 623/1.23, 1.38

(56) References Cited

U.S. PATENT DOCUMENTS

| | | | |
|---|---|---|---|
| 4,531,933 | 7/1985 | Norton et al. | 604/8 |
| 4,874,360 | 10/1989 | Goldberg et al. | 604/8 |
| 4,950,227 | * 8/1990 | Savin | 623/1.12 |
| 5,129,910 | 7/1992 | Phan et al. | 606/127 |
| 5,380,270 | 1/1995 | Ahmadzadeh | 604/9 |
| 5,380,335 | 1/1995 | Dormia | 606/127 |
| 5,551,954 | * 9/1996 | Buscemi | 623/1.38 |
| 5,599,291 | 2/1997 | Balbierz et al. | 604/8 |
| 5,647,843 | 7/1997 | Mesrobian et al. | 604/8 |
| 5,681,274 | 10/1997 | Perkins et al. | 604/8 |
| 5,746,745 | * 5/1998 | Abele et al. | 623/1.11 |
| 5,776,142 | * 7/1998 | Gonderson | 623/1.11 |
| 5,795,319 | 8/1998 | Ali | 604/8 |
| 5,830,217 | * 11/1998 | Ryan | 623/1.11 |
| 5,873,907 | * 2/1999 | Frantzen | 623/1.11 |
| 5,911,732 | * 6/1999 | Hojeibane | 623/1.11 |
| 5,984,963 | * 11/1999 | Ryan | 623/1.11 |

* cited by examiner

Primary Examiner—Michael J. Milano
(74) Attorney, Agent, or Firm—Gunster, Yoakley & Stewart, P.A.

(57) ABSTRACT

A stent is provided for decompressing an obstructed passage within the body such as a ureter to facilitate stone passage through a ureter or duct. An exemplary stent includes a flexible, elongate body that defines an open channel along the body. At least a portion of the body is made of a resilient material, wherein the open channel defines a void volume. A retaining or compressive force applied to the resilient material causes the void volume to be reduced, or maintained in a reduced state, until the retaining or compressive force is removed. A sleeve, a wire, or an adhesive soluble in liquid or dissolvable by ultrasound can provide the retaining force. The stent can be configured as a flexible, elongate body having elements distributed along the body that are movable from a first state to a second state to increase the diameter of the ureteral stent from a first diameter to a second diameter.

18 Claims, 4 Drawing Sheets

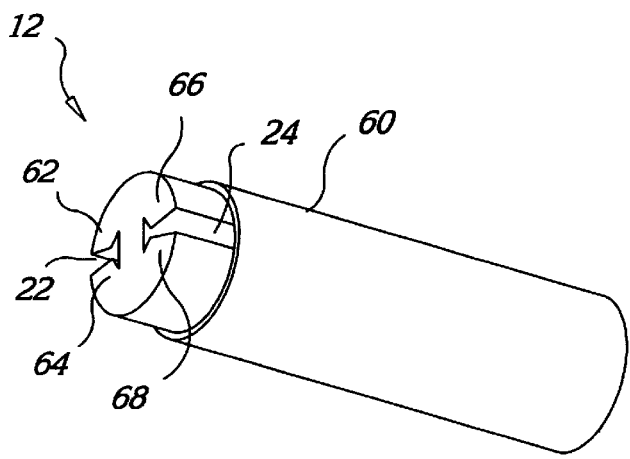
FIG. 10
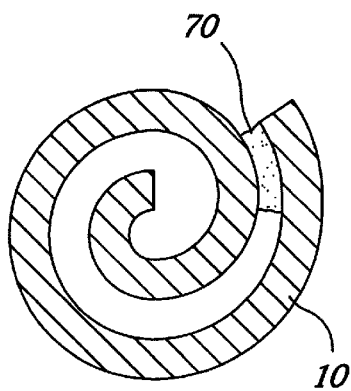
FIG. 11
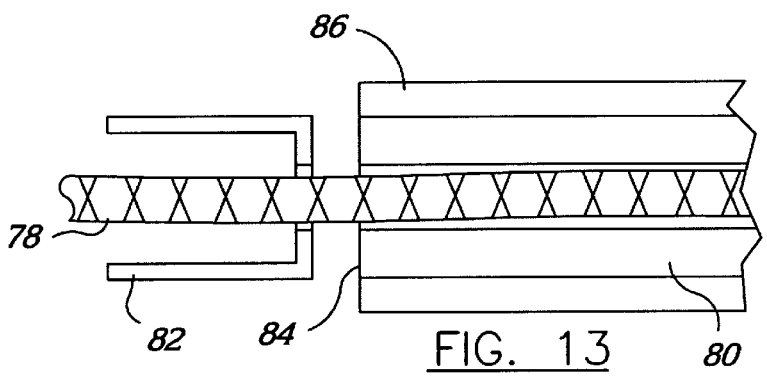
FIG. 13
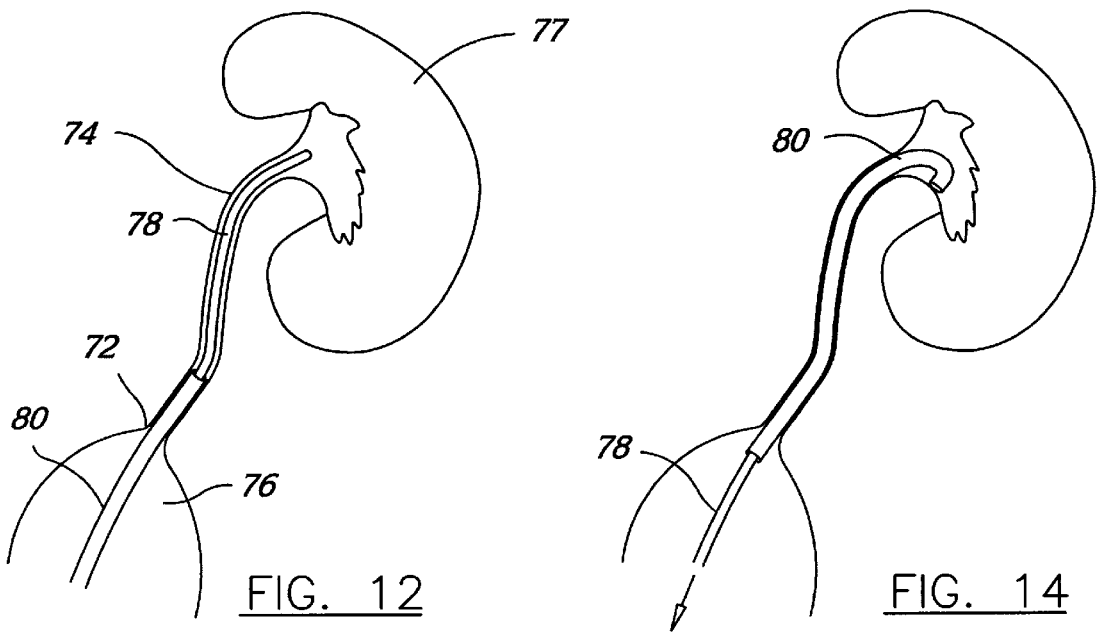
FIG. 12
FIG. 14

RADIALLY EXPANDING STENT

CROSS REFERENCE TO RELATED APPLICATIONS

Not applicable.

STATEMENT REGARDING FEDERALLY SPONSORED RESEARCH

Not applicable.

FIELD OF THE INVENTION

The present invention relates to a medical device, and more particularly to a stent.

BACKGROUND OF THE INVENTION

Calculus or stones in the urinary tract or kidneys usually arise because of the breakdown of a delicate balance in the body. Specifically, the kidneys must conserve water to function, but they must excrete materials that have a low solubility. These opposing requirements must be balanced during adaptation to diet, climate and activity. The problem is mitigated to some degree because urine contains substances that inhibit crystallization of stone forming minerals. However, when urine becomes supersaturated with insoluble materials, because excretion rates are excessive and/or because water conservation is extreme, crystals form and may grow and aggregate to form a stone.

Although small crystals are readily voided from the kidney with urine, the larger stones frequently become dislodged from the kidney and enter the ureter or occlude the uretero-pelvic junction, causing pain and obstruction. Although some stones can ultimately traverse the ureter, their passage usually produces pain and bleeding. Usually the pain is so severe that narcotic drugs are needed for its control.

Removal of stones from the kidneys or urinary tract can be effected medically or surgically. A well known surgical approach involves passing a flexible basket in a retrograde manner up the ureter from the bladder, and using the basket to capture the stones. Another surgical technique, known as extracorporeal lithotripsy, entails transmission of high-intensity shock waves from outside the body to fragment the stones within the body. The resulting stone fragments are then voided with urine. Yet another surgical technique, percutaneous ultrasonic lithotripsy, requires the passage of a rigid cystoscopy-like instrument in the renal pelvis through a small incision in the flank whereupon stones are broken up by a small ultrasound transducer and removed directly. Another surgical technique is laser lithotripsy via a uretero-scope. All of these procedures, which can be quite painful, are elaborate and expensive, and do not always result in complete removal of the stones and fragments.

Stents are used to decompress ureteral obstruction, ensuring that urine drains from the kidney to the bladder. It has also been recognized that placement of a stent within the ureter can help small stones and stone fragments to transit the ureter. In a typical procedure involving a stent, a guide wire is passed through the ureter to the renal pelvis. A hollow, flexible, cylindrical stent is then advanced with a pusher over the guide wire. The guide wire and pusher are then extracted from the stent and the body, leaving an open lumen for urine to pass through. However, because the lumen defined by the cylindrical stent is even smaller than the ureter itself, all but the smallest stones and sludge are precluded from passing therethrough. Some fragments are able to pass around the ureteral stent but larger stone fragments are unable to pass. In many cases, stone fragments often block the open stent passageway.

SUMMARY OF THE INVENTION

The present invention provides an improved stent that is not only well-suited for decompressing an obstructed passage within the body such as a ureter, but which is also configured to gently dilate and thus facilitate stone passage through a ureter or duct.

In an exemplary embodiment a stent includes a flexible, elongate body that defines an open channel along the body. At least a portion of the body is made of a resilient material, wherein the open channel defines a void volume. A retaining or compressive force applied to the resilient material causes the void volume to be reduced, or maintained in a reduced state, until the retaining or compressive force is removed. A sleeve, a wire, or an adhesive soluble in liquid or dissolvable by ultrasound can provide the retaining force.

In some embodiments, a flexible, elongate body includes elements distributed along the body and that are movable from a first state to a second state to increase the diameter of the ureteral stent from a first diameter to a second diameter.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 10 illustrates the stent of FIG. 3 compressed within a sleeve;

FIG. 11 shows the stent of FIG. 7 held in a compressed state with an adhesive;

FIG. 12 depicts a step in a procedure for placing a stent in accordance with the invention;

FIG. 13 illustrates the stent and associated components;

FIG. 14 shows removal of a guidewire from the stent;

DETAILED DESCRIPTION OF THE INVENTION

Figure 1:
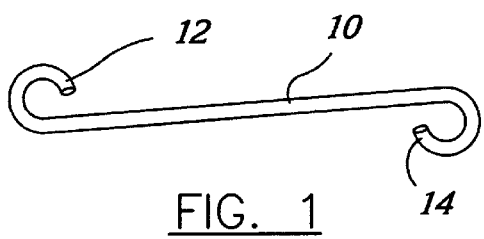
FIG. 1 is a perspective view of a stent in accordance with the present invention.

FIG. 1 is a perspective view of a stent in accordance with the invention. The stent includes a body 10 having a first end portion 12 and a second end portion 14. The stent body and end portions are flexible enough to assume a substantially linear configuration. However, in a static state, the end portions of the stent can assume a curved orientation as shown. Details regarding the features, exemplary dimensions, and use of the stent follow.

Figure 2:
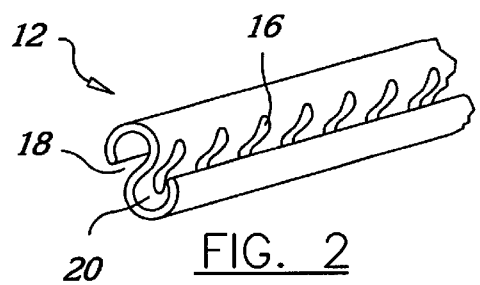
FIGS. 2–9D are detailed views of end portions of stents in accordance with present invention.

FIG. 2 is a detailed view of a straightened first end portion 12 of an exemplary stent. The opposite, second end portion 14 (not shown in FIGS. 2–8) is substantially identical to the first end portion. In this view, the stent body and end portions have an "S" shaped cross-section. Apertures 16 are provided along all or a portion of the length of the stent. Although the apertures 16 are shown as being elongate, they can also be oval or circular. The "S" shape of the stent body and end portions defines two longitudinal channels 18 and 20. As used herein, a channel is a path defined, or at least partially bound, by a portion of the stent body or end portions.

Figure 3:
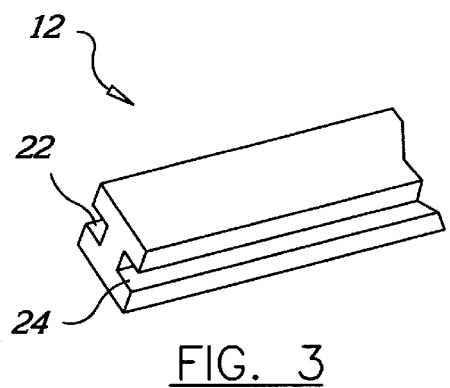

FIG. 3 illustrates the stent in an "I" configuration. Although not illustrated other than FIG. 2, apertures can be provided in this and all other stent configurations. The "I" shape defines two longitudinal channels 22 and 24.

Figure 4:
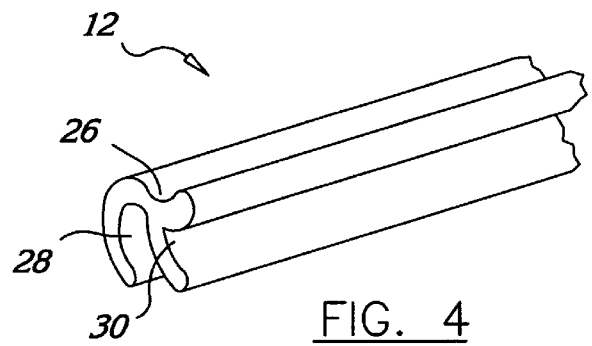

FIG. 4 illustrates the stent configured to provide three channels 26, 28 and 30.

Figure 5:
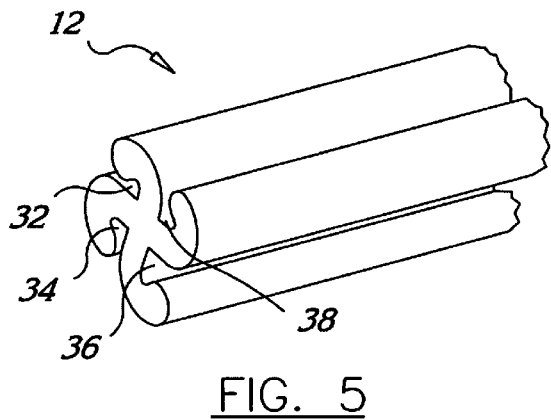

FIG. 5 illustrates the stent configured to provide four channels 32, 34, 36 and 38.

Figure 6:
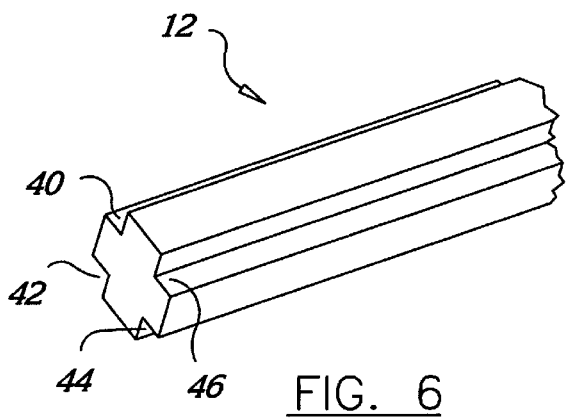

FIG. 6 also depicts the stent that defines four channels 40, 42, 44 and 46.

Figure 7:
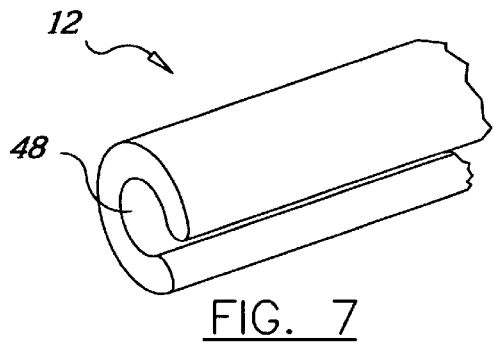

FIG. 7 depicts a stent with a single channel 48.

Figure 8:
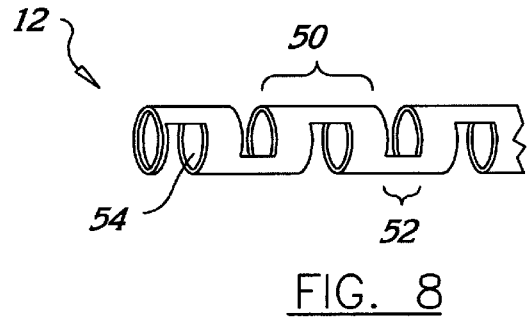

FIG. 8 illustrates a stent having segments 50 joined by linking regions 52 and defining a channel 54. In one embodiment, the linking regions bias or urge adjacent segments away from coaxial alignment. Thus, the channel(s) need not be linear and can be somewhat discontinuous or multiple channels are provided.

Figure 9A:
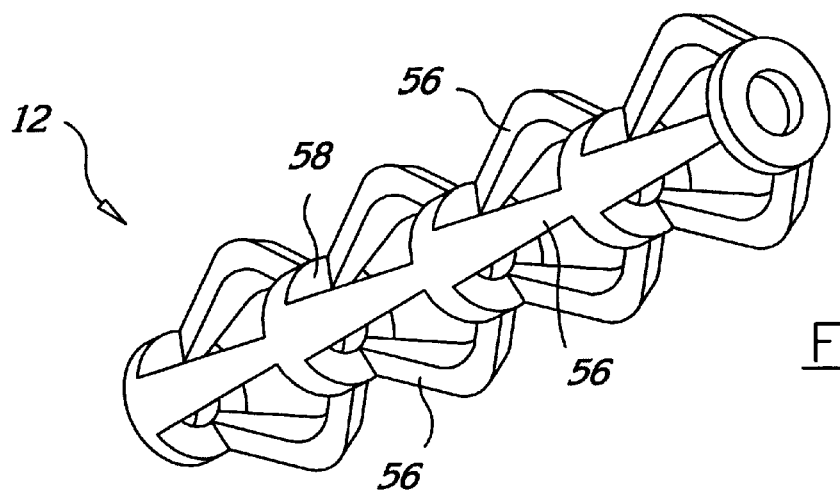
Figure 9B:
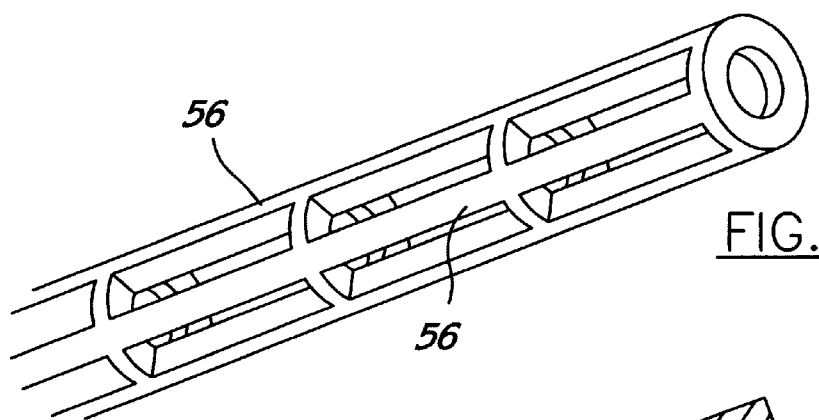
Figure 9C:
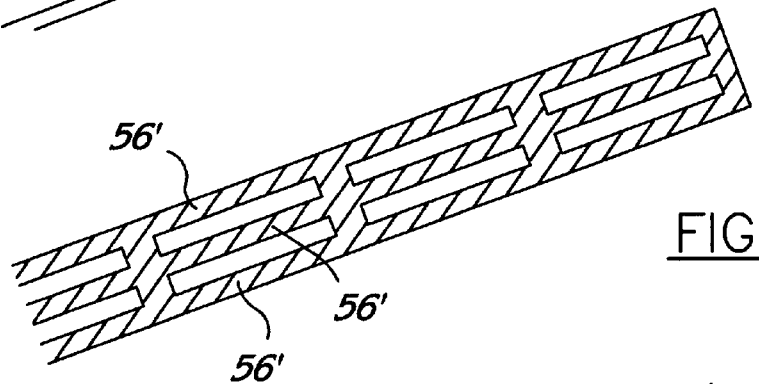
Figure 9D:
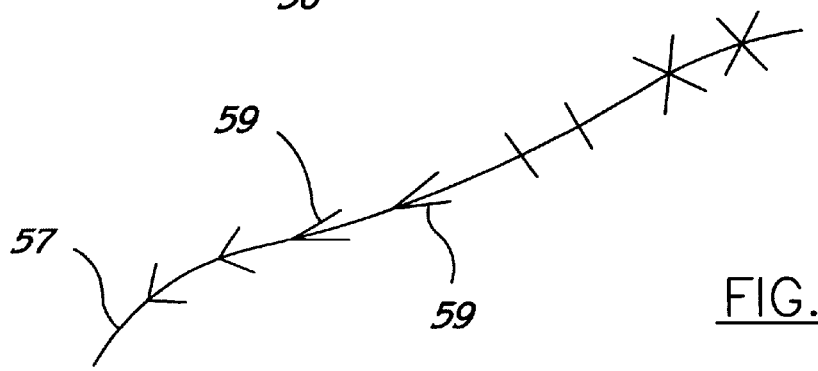

FIG. 9A illustrates a stent having resilient, substantially-longitudinal elements 56 connecting to disk-like structures 58. In the illustration, the elements 56 are bowed outward from a central axis of the stent to provide the stent with an undulating surface and alternating larger and smaller localized circumferential regions. FIG. 9B illustrates the stent of FIG. 9A with the elements 56 in a substantially linear or non-bowed configuration. FIG. 9C depicts yet another embodiment of the stent, wherein the stent is substantially planar in a first configuration as shown. In a second configuration, elements 56' bow outward as shown with respect to the stent of FIG. 9A. FIG. 9D illustrates yet another embodiment, wherein an elongate flexible body is provided with barbs 59 that can be transitioned from a reduced diameter configuration 59 to a larger diameter configuration. In the illustration, barbs 59 are shown in different configurations and states. The stents of FIGS. 9A–D can be transitioned from a uniform/reduced diameter configuration to a nonuniform/larger diameter configuration by compressing the stent longitudinally, or by removing a restraining force from outwardly biased elements 56 or 56'. In exemplary embodiments a restraining force is provided by a sleeve as shown with respect to FIG. 10 or with adhesives as described below with respect to FIG. 11.

FIG. 10 depicts the stent of FIG. 3 within a sleeve 60. Because at least a portion of the stent is flexible, such as body portions 62, 64, 66 and 68 that define the channels 22 and 24, the stent can be folded into a sleeve having a smaller diameter than the stent in its unfolded state. If the material of the stent is compressible, the stent can be placed into an even smaller diameter sleeve. The sleeve 60 thus can serve at least two important functions: it temporarily reduces the diameter of the stent and, until removal, it provides a smooth exterior surface. Both of these features facilitate deployment of the stent as described below.

Alternatively, as shown in FIG. 11, the stent in a configuration such as shown in the sectional end view of FIG. 7 can be folded or rolled and held in that configuration with a water or acid soluble adhesive 70. Thus, when the adhesive dissolves, the stent unfolds or unrolls.

Exemplary stents are made of silicone and have lengths in the range of 22 to 32 centimeters for adults and about 16 to 18 centimeters for children. However, the length of the stent can be modified as required. A stent can have a diameter of about 7.0 FR for placement within a ureteral orifice 3 millimeters in diameter. Stents as described herein are well suited for removal of a stone up to 10 millimeters in diameter.

FIG. 12 illustrates a step of an exemplary procedure, wherein a cystoscope has been used to find the orifice 72 of the ureter 74 leading between the bladder 76 and a kidney 77. A flexible wire 78, such as is known in the art, has been guided through the orifice 72 and into the ureter. A stent 80 in accordance with the invention is selected, placed over the wire 78, and passed into the ureter 74.

As illustrated in FIG. 13, a pusher 82 can be placed over the wire 78 and pressed against the proximal end 84 of the stent 80. In this illustration, the stent 80 is compressed within a sleeve 86.

The pusher 82, if used, and the flexible wire 78 are then removed, as shown in FIG. 14, and the stent is left in place. If a sleeve is used, it can also be removed from the stent. However, as removal of a sleeve from a stent can be difficult, especially if the stent or portions thereof are compressed by the sleeve, the present invention provides a sleeve that degrades or dissolves to release the stent therefrom. In an exemplary embodiment, the sleeve is made of a material the dissolves in urine within a few hours. The material can be a water, base or acid soluble material such as sugars, polydioxanone, polyglecaprone 25, polyglactine, gelatine sponge, hylauronan-benzyl ester hyaluronic acid, cyanoacrylate, chromic suture material and polyglycolic acid. Additionally, the material can be dissolvable by ultrasound.

Figure 15:
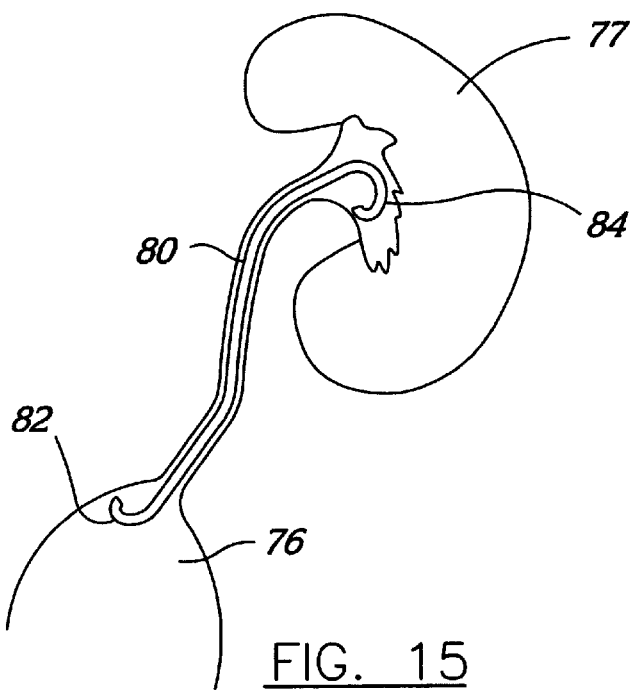
FIG. 15 illustrates the stent in position within a dilated ureter.

When the wire and sleeve are removed, the relatively unconfined ends of the stent form a retention shape, such as by curling to form a "double-J," as is known in the art, and as shown in FIG. 15. A first curled end portion (or "J") anchors a first end 82 of the stent 80 within the bladder 76 and a second curled end portion anchors a second end 84 of the stent within the kidney 77.

Figure 16:
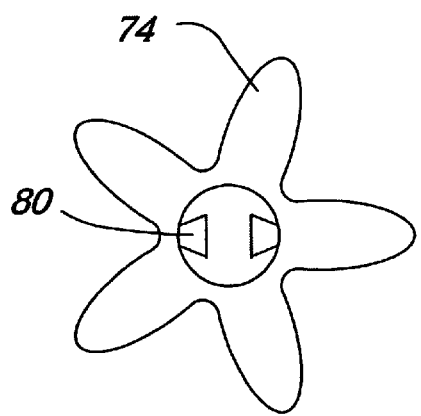
FIG. 16 illustrates in stent within an undilated ureter.
Figure 17:
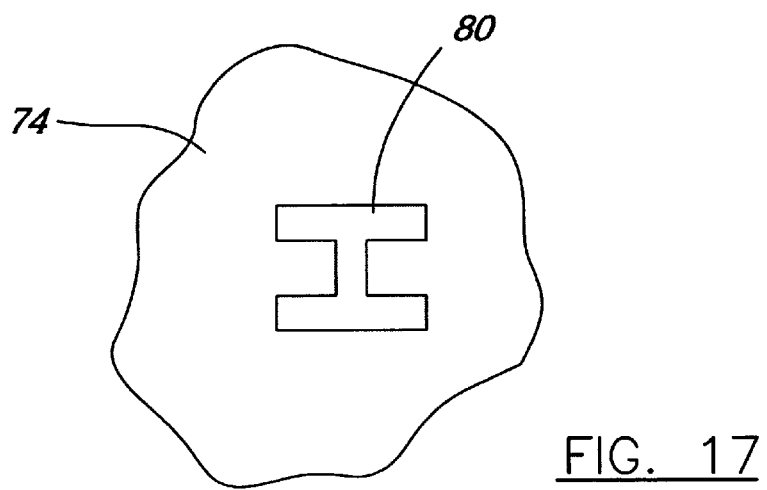
FIG. 17 illustrates the stent of FIG. 16, after the ureter has dilated.

When the stent 80 is in place, the ureter 74 dilates around the stent naturally from a normal state as shown in FIG. 16 to an increased diameter or dilated state as illustrated in FIG. 17. The effect is particularly evident when the stent selected for insertion is a radially expandable stent. Although a stone may not have been able to pass through an undilated ureter, after dilation the stone (depending on its size) is able to pass through the increased diameter ureter. After the stone(s) have been eliminated from the body, the stent is removed from the body. Any stones trapped in the channel(s) are removed with the stent. The channel(s) help to maximize a flow path for urine and they provide an enlarged path for the stones to wash into the bladder. By contrast with known cylindrical stents, the open cross-section of the present stent is not easily clogged. Furthermore, the open channel configurations do not readily become pinched closed as do known complete, cylindrical, catheter-like tubes.

Instead of removing the stent using techniques known to those skilled in the art, the stent can be fabricated from a material that degrades into small pieces or dissolves so that it can be passed with urine. The stent can be made of a urine, water, acid, or base soluble material such as sugar, polydioxanone, polyglecaprone 25, polyglactine, gelatine sponge, hylauronan-benzyl ester hyaluronic acid, or cyanoacrylate. Alternatively, the stent can dissolve when exposed to ultrasound. An exemplary stent dissolves completely within a week or two. Even if dissolution of the stent begins when the sleeve is removed, the rate of deterioration is slow enough so that the stent will perform its intended purpose.

In addition to placement in a ureter, the stent in accordance with the invention can be therapeutically effective with respect to obstruction, stricture and external compression of any tubular structure within the body including airways, bile ducts, pancreatic ducts, the bowel, blood vessels and the urethra.

It will be appreciated by persons skilled in the art that the present invention is not limited to what has been particularly shown and described herein above, and that the drawings are not to scale. A variety of modifications and variations are possible in light of the above teachings without departing from the scope and spirit of the invention, which is limited only by the following claims.

What is claimed is:

1. A uteral stent comprising:
   a flexible, elongate body having a first end, a second end, and a longitudinal axis, the flexible, elongate body defining an a first continuous, outwardly-open channel that extends longitudinally from the first end of the body to the second end of the body, wherein the longitudinal axis of the body is substantially parallel to the channel.

2. The stent of claim 1, further comprising a second continuous, outwardly-open channel that extends longitudinally from the first end of the body to the second end of the body, wherein at least a portion of the body is made of a resilient material.

3. The stent of claim 1, further comprising an elongate sleeve that defines a passage for receiving the stent and completely encloses the body except at its first and second ends.

4. The stent of claim 3, wherein the sleeve is made of a flexible plastic.

5. The stent of claim 1, wherein the stent is soluble.

6. The stent of claim 5, wherein the stent is made of a material selected from the group consisting of sugar, polydioxanone, polyglecaprone 25, polyglactine, gelatine sponge, hylauronan-benzyl ester hyaluronic acid, cyanoacrylate, chromic suture material, and polyglycolic acid.

7. The stent of claim 1, wherein the body has an "S" shaped cross-section.

8. The stent of claim 1, wherein the body has an "C" shaped cross-section.

9. The stent of claim 1, wherein the body has an "I" shaped cross-section.

10. The stent of claim 1, wherein the body has an "Y" shaped cross-section.

11. The stent of claim 1, wherein the body has an "+" shaped cross-section.

12. A ureteral stent comprising:
    a flexible, elongate body having a first end and a second end, the flexible elongate body defining an a first continuous, outwardly-open channel that extends longitudinally from the first end of the body to the second end of the body.
    a second continuous, outwardly-open channel that extends longitudinally from the first end of the body to the second end of the body, wherein at least a portion of the body is made of a resilient material; and
    an adhesive binding a portion of the body to another portion of the body to maintain the stent in a compressed state.

13. The stent of claim 12, wherein the adhesive is soluble in a liquid.

14. The stent of claim 12, wherein the adhesive dissolves when exposed to ultrasound energy.

15. The stent of claim 13, wherein the adhesive is made of a material selected from the group consisting of sugar, polydioxanone, polyglecaprone 25, polyglactine, gelatine sponge, hylauronan-benzyl ester hyaluronic acid, cyanoacrylate, chromic suture a rial, and polyglycolic acid.

16. The stent of claim 3, wherein the adhesive dissolves when exposed to ultrasound energy.

17. A ureteral stent comprising:
    a flexible, elongate body having a first end and a second end, the flexible elongate body defining an a first continuous, outwardly-open channel that extends longitudinally from the first end of the body to the second end of the body;
    an elongate sleeve that defines a passage for receiving the stent;
    wherein the sleeve is soluble in a liquid.

18. A ureteral stent comprising:
    a flexible, elongate body having a first end and a second end, the flexible elongate body defining an a first continuous, outwardly-open channel that extends longitudinally from the first end of the body to the second end of the body;
    an elongate sleeve that defines a passage for receiving the stent;
    wherein the sleeve is made of a material selected from the group consisting of sugar, polydioxanone, polyglecaprone 25, polyglactine, gelatine sponge, hylauronan-benzyl ester hyaluronic acid, cyanoacrylate, chromic suture material, and polyglycolic acid.

* * * * *

UNITED STATES PATENT AND TRADEMARK OFFICE
CERTIFICATE OF CORRECTION

PATENT NO.      : 6,214,037 B1
DATED           : April 10, 2001
INVENTOR(S)     : Mitchell et al.

It is certified that error appears in the above-identified patent and that said Letters Patent is hereby corrected as shown below:

Column 5,
Line 17, replace "A uteral stent comprising:" with -- A ureteral stent comprising:" --

Signed and Sealed this

Eighth Day of April, 2003

JAMES E. ROGAN
*Director of the United States Patent and Trademark Office*